United States Patent [19]

Tsukada et al.

[11] Patent Number: 4,890,919
[45] Date of Patent: Jan. 2, 1990

[54] ATOMIC ABSORPTION SPECTROPHOTOMETER

[75] Inventors: Masamichi Tsukada, Ibaraki; Konosuke Oishi, Mito; Katsuhito Harada; Toyoharu Okumoto, both of Katsuta, all of Japan

[73] Assignee: Hitachi, Ltd., Tokyo, Japan

[21] Appl. No.: 140,715

[22] Filed: Jan. 4, 1988

[30] Foreign Application Priority Data

Jan. 7, 1987 [JP] Japan .................................. 62-428

[51] Int. Cl.⁴ .............................................. G01N 21/74
[52] U.S. Cl. .............................................. 356/312
[58] Field of Search ........................ 356/312, 244, 319

[56] References Cited

U.S. PATENT DOCUMENTS 4,076,421  2/1978  Kishner .......................... 356/236 X
4,283,934  8/1981  Siess ................................. 73/1 F
4,339,201  7/1982  Yasuda et al. ...................... 356/312

OTHER PUBLICATIONS

Watne et al., *Applied Spectroscopy*, vol. 30, No. 1, Jan.-/Feb. 1976, pp. 71 and 72.

*Primary Examiner*—F. L. Evans
*Attorney, Agent, or Firm*—Antonelli, Terry & Wands

[57] ABSTRACT

An atomic absorption spectrophotometer is disclosed in which, in order to detect the temperature of a graphite cuvette correctly on the basis of the radiation emitted from the inner wall of the graphite cuvette, the above radiation and the measuring light emitted from a hollow cathode lamp are both taken out by the same optical members, and then the radiation is separated from the measuring light, to be detected and used for measuring the temperature of the graphite cuvette.

8 Claims, 3 Drawing Sheets

ATOMIC ABSORPTION SPECTROPHOTOMETER

BACKGROUND OF THE INVENTION

The present invention relates to an atomic absorption spectrophotometer using a graphite cuvette (namely, an absortion cell made of graphite), and more particularly to an atomic absorption spectrophotometer which can accurately detect the temperature of the graphite cuvette used.

In an atomic absorption spectrophotometer using a graphite cuvette, a metallic element contained in a sample is atomized by heat from the graphite cuvette, and measuring light from a hollow cathode lamp is selectively absorbed by the atomized metallic element. Thus, the metallic element can be quantitatively determined on the basis of the measured absorbance. In more detail, the measuring light from the hollow cathode lamp passes through the graphite cuvette and is then led to a spectroscope through an optical element (that is, a mirror or lens), to extract only a wavelength component which can be absorbed by the metallic element. Further, an electric current is supplied to the graphite cuvette, to heat and atomize the sample with the aid of the Joule heat which is generated in the graphite cuvette. In such an operation, the reproducibility of an increasing rate of graphite sample atomizing temperature have a great influence on the result of analysis, and hence it is required to detect the temperature of the graphite cuvette accurately. A temperature control device has been proposed in U.S. Pat. No. 4,283,934. In this device, a detector is disposed in the vicinity of a graphite cuvette (namely, a graphite tube) to detect the thermal radiation from the graphite cuvette, and a current supplied to the graphite cuvette is changed in accordance with the output of the detector, to set an atomizing temperature to a desired value. In the above device, however, when the sample is heated and atomized, the detector is contaminated with various substances from the graphite cuvette, since the detector is disposed in the vicinity of the graphite cuvette. That is, the detector is contaminated with the vapor of the sample, or the vapor of an acid, alkali, or others contained in the sample. Further, carbon powder is scattered from the graphite cuvette, and deposited on the detector. That is, the detector is contaminated with the carbon powder. Such contamination proceeds with time, and reduces the transmissivity of the light receiving surface of the detector. Thus, it is impossible that the detector receives the radiation from the graphite cuvette correctly, and the correctness of temperature control is lost with time.

SUMMARY OF THE INVENTION

It is an object of the present invention to provide an atomic absorption spectrophotometer which includes a device capable of accurately detecting the temperature of a graphite cuvette for a long time, to eliminate the drawback of the prior art.

Thermal radiation is generated not only at the outer periphery of the graphite cuvette but also at the inner wall thereof. If the radiation emitted from the inner wall of the graphite cuvette can be taken out by an optical system for measuring light which is emitted from a hollow cathode lamp, and then discriminated from the measuring light, a temperature detecting device will be obtained which is not contaminated with the substances from the graphite cuvette.

In more detail, the radiation from the inner wall of a central portion of a tubular graphite cuvette travels outwards along the center axis of the tubular cuvette through both ends thereof. While, the measuring light from the hollow cathode lamp passes through the center of the graphite cuvette. Hence, the optical axis of the above radiation agrees with that of the measuring light. In order to discriminate the radiation from the measuring light, it is necessary to take out both the radiation and the measuring light by an optical system for the measuring light, and to separate the radiation from the measuring light at a predetermined position where the radiation is scarcely mixed with the measuring light, that is, a position proximate to a slit, on which the measuring light is focused. In the vicinity of the slit, the measuring light from the hollow cathode lamp travels in a narrow region including the optical axis, as in the central portion of the graphite cuvette, and the radiation from the inner wall of the central portion travels in a cylindrical region which exists outside of the measuring light beam. At a position remote from the slit, the radiation is mixed with the measuring light, and thus it is very difficult to discriminate the radiation from the measuring light. In the vicinity of the slit, on which the measuring light is focused, the radiation beam from the inner wall of the graphite cuvette has the form of a cylinder disposed on the outside of the measuring light beam. Accordingly, when a discriminating member which has a through hole for transmitting the measuring light, is inserted in an optical path at a position proximate to the slit, the radiation can be separated from the measuring light. When the radiation thus obtained is measured by a detector, the temperature of the graphite cuvette can be accurately detected.

DESCRIPTION OF THE PREFERRED EMBODIMENTS

Figure 1:
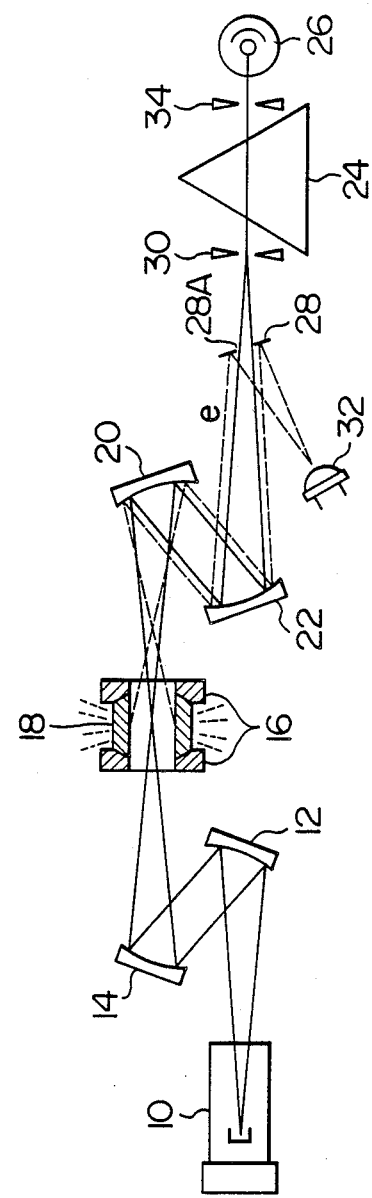
FIG. 1 is a schematic diagram showing the optical system of an embodiment of an atomic absorption spectrophotometer according to the present invention.

FIG. 1 shows the optical system of an embodiment of an atomic absorption spectrophotometer according to the present invention.

Figure 4:
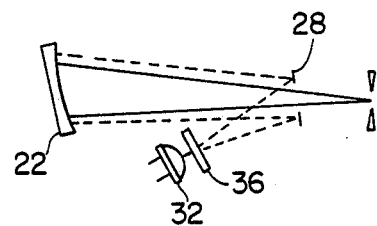
FIGS. 4, 5 and 6 illustrate different separation and detection arrangements according to other embodiments of the present invention.
Figure 5:
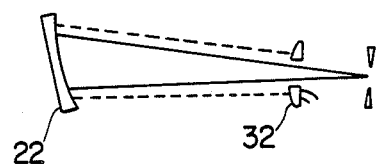
Figure 6:
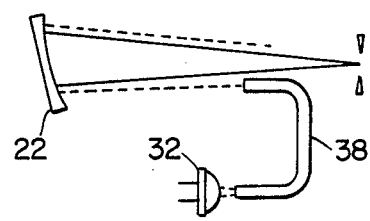

Referring to FIG. 1, measuring light from a hollow cathode lamp 10 is focused on a point within a tubular graphite cuvette 18 by mirrors 12 and 14, and is then led to a spectroscope 24 through mirrors 20 and 22. The measuring light emerging from the spectroscope 24 is received by a photomultiplier 26. Both ends of the tubular graphite cuvette 18 are held by a pair of electrodes 16. When the measuring light passes through the graphite cuvette 18 kept at a high temperature, constituent atoms of a sample to be analyzed absorb the measuring light. The spectroscope 24 is set so that only that wavelength component of the measuring light which can be absorbed by a desired element contained in the sample, is received by the photomultiplier 26. Thus, the desired element can be quantitatively determined on the basis of the absorbance of the above wavelength component. Radiation which is emitted by the inner wall of the graphite cuvette 18 and designated by reference character e, is focused on a position by the mirrors 20 and 22. Further, a reflecting plate 28 is disposed between the mirror 22 and an entrance slit 30 for the spectroscope 24 so that the radiation e reflected from the reflecting plate 28 goes away from the optical axis of the measuring light. A through hole 28A for transmitting the measuring light is provided in a central portion of the reflecting plate 28, and a sensor array 32 acting as a temperature detector is disposed at a position, on which the radiation e reflected from the reflecting plate 28 and having a ring-shaped cross section is focused. The quantity of the radiation e is far greater than the quantity of the measuring light. Hence, it is not required to use an expensive mirror having an aperture as the reflecting plate 28, but a metal plate plated with, for example, nickel or chromium can be used as the reflecting plate 28. In a case where the graphite cuvette 18 is heated to a low temperature, that is, a temperature lower than 1,000° C, that wavelength component of the measuring light which is emitted from neon introduced into the hollow cathode lamp, may be mixed with the radiation e by scattering or others. In this case, it is preferred to dispose an optical filter 36 as illustrated in FIG. 4 for cutting a spectral component which is emitted from neon and has a wavelength of 632.8 nm, in front of the sensor array 32. Alternatively, a sensor array 32 for detecting the radiation e may be mounted at the position of the reflecting plate 28 as illustrated in FIG. 5, or an optical fiber 38 may be used in place of the reflecting plate 28 to discriminate the radiation e from the measuring light as illustrated in FIG. 6. Incidentally, in FIG. 1, reference numeral 34 designates an exit slit for transmitting only a desired wavelength component.

Although the measuring light and a part of the radiation e pass through the through hole 28A of the reflecting plate 28, the radiation e is removed by the spectroscope 24, and thus will have no effect on the absorbance measurement.

Figure 2A:
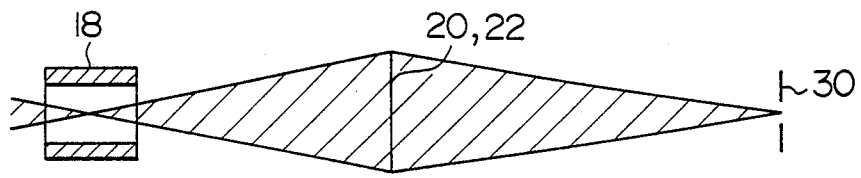
FIGS. 2a to 2c are schematic diagrams for explaining how the radiation from the inner wall of a graphite cuvette is discriminated from measuring light.
Figure 2B:
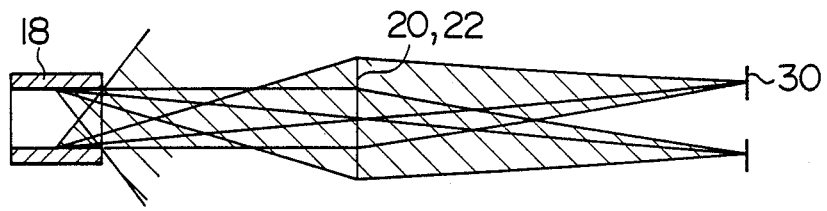
Figure 2C:
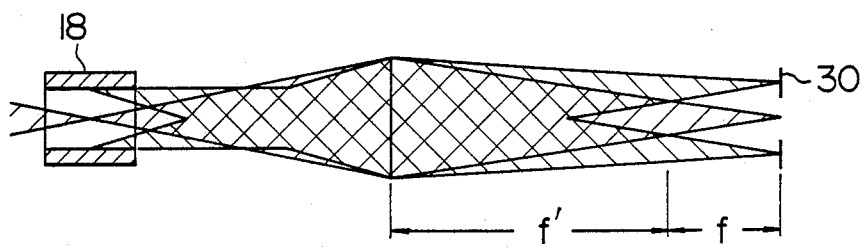
Figure 3:
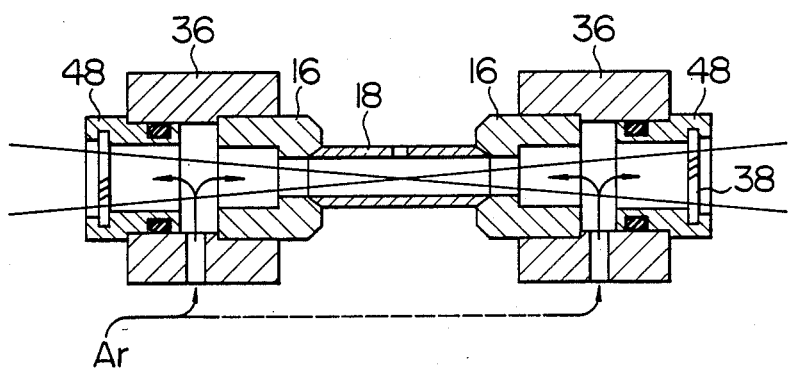
FIG. 3 is a sectional diagram showing an atomizing portion in detail.

FIGS. 2a to 2c are sectional diagram taken along the optical axis and showing light beams which extend from the graphite cuvette to the exit slit through optical elements 20 and 22. In more detail, FIG. 2a shows only the measuring light beam from the hollow cathode lamp. As shown in FIG. 2a, the measuring light beam is focused on the center of the graphite cuvette 18, and is again focused on the entrance slit 30 through the optical elements 20 and 22, to be led to the spectroscope 24. FIG. 2b shows a radiation beam which is emitted from the inner wall of the graphite cuvette in directions toward the spectroscope 24. Strictly speaking, FIG. 2b shows a maximum radiation beam which is emitted from the inner wall of a central portion of the graphite cuvette 18 and can pass through the optical elements 20 and 22. As can be seen from FIG. 2b, the radiation beam is focused on an entrance slit plate at an annular region thereof. Further, as shown in FIG. 2b, the radiation from the inner wall of the graphite cuvette departs from an end aperture of the graphite cuvette in various directions. Accordingly, it seems that the radiation can be taken out at a position which is located in the vicinity of the graphite cuvette or located midway between the graphite cuvette and the optical elements 20 and 22, without being mixed with the measuring light. However, as is apparent from FIG. 3 which shows an atomizing portion in detail, the graphite cuvette 18 has the form of a long, narrow tube, and not only an electrode 18 but also a holding member 48 for holding an argon blocking window is inserted into each electrode receptacle 36. As a result, it is impossible to make the diameter of the radiation beam far greater than that of the measuring light beam. Accordingly, it is very difficult to discriminate the radiation beam from the measuring light beam at a position located in the vicinity of the atomizing portion. FIG. 2c shows an actual state, in which the measuring light beam and the radiation beam coexist. Referring to FIG. 2c, it is very important that the measuring light is first focused on the center of the graphite cuvette, and thus both an image of the center of the graphite cuvette and an image of the inner wall of the graphite cuvette are formed on the entrance slit plate by the same optical elements. Thus, as shown in FIG. 2c, the measuring light beam and the radiation beam do not mix in a range f. In the range f, the measuring light travels in a narrow region including the optical axis, and the radiation travels in a cylindrical region which exists on the outside of the measuring light beam. Accordingly, the range f is used for discriminating the radiation beam from the measuring light beam. Although the radiation beam is mixed with the measuring light beam in a range f', only the radiation beam exists in a peripheral portion as shown in FIG. 2c. Hence, in a case where it is required to separate only part of the radiation from the measuring light beam, the range f' can be used.

The present embodiment is constructed as mentioned above, and hence can control the current supplied to the graphite cuvette, in the following manner. That is, as soon as an atomizing stage is started, a maximum current of 400 amp is supplied to the graphite cuvette to heat the graphite cuvette, thereby emitting radiation therefrom. The radiation from the graphite cuvette is monitored, and the current supplied to the graphite cuvette is controlled so that the intensity of the radiation is maintained at a value corresponding to a predetermined atomizing temperature. Thus, the atomization of a sample and the atomic absorption due to the sample are efficiently carried out. Accordingly, the present embodiment is high in sensitivity, and short in atomizing time. Thus, the degradation of graphite cuvette with time is reduced, and the life of the graphite cuvette is increased.

We claim:

1. An atomic absorption spectrophotometer comprising:
    a light source for emitting measuring light;
    a graphite cuvette for atomizing a sample;
    first optical means for focusing the measuring light from said light source, on a position within said graphite cuvette;
    second optical means for focusing the measuring light having passed through said graphite cuvette, on a slit;
    separation means disposed between said second optical means and said slit for separating radiation which is emitted from the inner wall of said graphite cuvette, from the measuring light with substantially no reduction of the energy of the measuring light;
    detection means for detecting the radiation which has been separated form the measuring light;
    a spectroscope for separating the measuring light having passed through said slit, into spectral components; and a detector for detecting light which emerges from said spectroscope;

wherein said separation means includes a reflecting plate having a through hole at a central portion thereof and being disposed between said second optical means and said slit, and the measuring light passes through said through hole.

2. An atomic absorption spectrophotometer according to claim 1, wherein each of said first and second optical means is made up of mirrors.

3. An atomic absorption spectrophotometer according to claim 1, wherein the radiation having been separated from the measuring light is detected by said detection means through an optical filter for cutting a wavelength component which is emitted from said light source.

4. An atomic absorption spectrophotometer according to claim 3, wherein said optical filter cuts a wavelength component emitted from neon.

5. An atomic absorption spectrophotometer according to claim 1, wherein said separation means enables separation of the measuring light and said radiation without effecting beam splitting.

6. An atomic absorption spectrophotometer comprising:
a light source for emitting measuring light;
a graphite cuvette for atomizing a sample;
first optical means for focusing the measuring light from said light source, on a position within said graphite cuvette;
second optical means for focusing the measuring light having passed through said graphite cuvette, on a slit;
separation means disposed between said second optical means and said slit for separating radiation which is emitted from the inner wall of said graphite cuvette, from the measuring light with substantially no reduction of the energy of the measuring light;
detection means for detecting the radiation which has been separated from the measuring light;
a spectroscope for separating the measuring light having passed through said slit, into spectral components; and
a detector for detecting light which emerges from said spectroscope;
wherein said separation means includes an optical fiber.

7. An atomic absorption spectrophotometer according to claim 6, wherein said separation means enable separation of the radiation and the measuring light without effecting beam splitting.

8. An atomic absorption spectrophotometer according to claim 6, wherein each of said first and second optical means is made up of mirrors.

* * * * *